United States Patent [19]
Plijter et al.

[11] Patent Number: 6,083,538
[45] Date of Patent: *Jul. 4, 2000

[54] BREAD IMPROVING COMPOSITION

[75] Inventors: Johannes Josef Plijter, Wateringen; Gabriel Marinus Henricus Meesters, Delft, both of Netherlands

[73] Assignee: DSM N.V., Netherlands

[ * ] Notice: This patent issued on a continued prosecution application filed under 37 CFR 1.53(d), and is subject to the twenty year patent term provisions of 35 U.S.C. 154(a)(2).

[21] Appl. No.: 09/120,420

[22] Filed: Jul. 22, 1998

[30] Foreign Application Priority Data

Jul. 22, 1997 [EP] European Pat. Off. .............. 97202292

[51] Int. Cl.$^7$ .............................. A21D 10/00; A21D 2/08
[52] U.S. Cl. ................................. 426/20; 426/94; 426/98; 426/549
[58] Field of Search ..................................... 435/198, 187; 424/490, 94.3; 426/20, 89, 98, 94, 289, 549

[56] References Cited

U.S. PATENT DOCUMENTS

| | | | |
|---|---|---|---|
| 4,740,469 | 4/1988 | Nishinaka | 435/187 |
| 4,849,227 | 7/1989 | Cho | 424/498 |
| 5,258,132 | 11/1993 | Kamek et al. | 252/94 |
| 5,846,798 | 12/1998 | Paatz et al. | 435/187 |

FOREIGN PATENT DOCUMENTS

| | | |
|---|---|---|
| 0 304 332 | 2/1989 | European Pat. Off. . |
| 0 585 988 | 3/1996 | European Pat. Off. . |
| WO 94/04035 | 3/1994 | WIPO . |
| WO 94/26883 | 11/1994 | WIPO . |
| WO 97/12958 | 4/1997 | WIPO . |

*Primary Examiner*—Keith Hendricks
*Attorney, Agent, or Firm*—Morrison & Foerster LLP

[57] ABSTRACT

This invention relates to a coated lipase granule comprising lipase coated with a material which is impervious to lipid.

13 Claims, No Drawings

BREAD IMPROVING COMPOSITION

The present invention relates to a novel bread improving composition and its uses.

In recent years enzymes have been used to an increasing extent as highly useful aids to facilitate baking processes and improve the quality of baked products.

The use of lipase (EC 3.1.1.3) combined with other enzymes in baking is known (see European Patent EP 0585 988 B1 or International application WO 94/04035). Lipase catalyses the hydrolysis of triglycerides (lipids) into mono- and diglycerides and free fatty acids. Whereas the amount of such lipids is relatively low (0.5–2%) in the flour made from most cereal crops. Many compositions used in the baking industry to improve the properties of bread contain substantial amounts of fats. We have found that lipase, when present in such compositions, generates free fatty acids during storage which strongly shortens the shelf-life of the compositions.

Coating of enzyme granules is used to prevent the formation of enzyme dust, especially for enzymes used in detergents. The enzyme granules may be coated with a material which forms a film. Such a coating is used to prevent dust formation, rather than to form a barrier between the enzyme and for other compounds, such as fats.

Theoretical calculations show that such a coating would not prevent fat penetrating into the enzyme particle.

Lipase is an enzyme which is still active at very low water concentrations. Since the compositions added to improve bread properties have a concentration of water higher than the water concentrations at which lipase is active, lipase in these compositions would be active.

Although the diffusion coefficients of lipids in the coating material of enzyme particles is not known, one can estimate the value of these coefficients based on the coefficients known for other materials.

For proteins (e.g. enzymes) in cheese the diffusion constant is $10^{-12}$ m$^2$/s. So the lowest diffusion coefficient for lipids would be in the order of $10^{-15}$ m$^2$/s (this is two orders of magnitude lower than diffusion coefficient in bitumen). In reality the diffusion constant of lipids in the coating material is probably higher than this.

The thickness of the coating on the granule of course varies, but the upper limit is in the range of 25 $\mu$m.

Based on the assumption that the effective diffusion coefficient is $10^{-15}$ m$^2$/s one can calculate the distance within the coating at which the lipid concentration is halved per unit time. As an example for one second this distance is 32 nm, for one hour 2 $\mu$m. Similar calculations for 25 $\mu$m of coating material the upper limit of the thickness of the coating layer show that after 7 days the lipid concentration at the lipase is already half of the concentration of that in the composition. Some granules have a coating which is less than 25 $\mu$m. Therefore for these the time needed for the lipid concentration at the lipase to be half that in the composition would be much shorter, since the time and distance are related to each other by a power factor of 2 (so either square or square root depending on the formulation of the equation used).

From further calculations one can conclude that even after one day lipid has already reached the enzyme inside the coated particle and therefore the lipid break down products which cause rancidity are being formed. However the times which are being estimated in these calculations are the upper limits for how long it will be to the start of lipase activity. In practice one should expect shorter times, as the diffusion coefficient is probably at least one order of magnitude larger. In addition, there is variation in the thickness of the coating, therefore it will often be much less than 25 $\mu$m and hydrolysis of the lipid will begin as soon as any lipid has reacted the enzyme.

Therefore, the use of materials which form films to coat the lipase would not be expected to solve the problem of how to substantially reduce fat hydrolysis.

Surprisingly, we have found a coat formulation for the lipase which substantially reduces the amount of fat degradation which occurs during the storage period of the composition. In addition, the enzyme becomes fully active as soon as water is added by the baker in the mixer.

We found that the coat formulation for the lipase prevents the occurrence of rancidity when the lipase granules are added to compositions containing lipids. This is surprising because as discussed above understanding of the physical and biochemical aspects of the system would lead one to expect that rancidity would occur.

Therefore, the lipase granule is coated with a suitable coating layer which substantially prevents fat degradation during storage. Suitable coating materials are sugars, starch, hydrolysed starch, starch derivatives, polyols such as polyethylene glycol, cellulose acetate phthalate, polyvinyl acetate phthalate, hydroxypropyl methylcellulose phthalate, and cellulose or cellulose based compounds containing e.g. hydroxypropylcellulose, methyl cellulose, hydroxypropyl methyl cellulose and/or hydroxyethyl cellulose, and mixtures thereof. Optionally coating improving agents may be added. The lipase can, for instance, be produced as a granule or can be transferred onto a core material (e.g. using spraying technologies). Both methods result in enzyme particles having a granule shape. The production of such enzyme granules is known.

In general the core materials used would be of food grade quality. NaCl is an example of a core material which may be used.

In general the amounts of coating material will be 1 to 25 w/w % of the final enzyme granule, preferably 3 to 15 w/w %.

The coated lipase can be added to compositions to improve the properties of bread. Normally bread is made from a dough comprising flour, water, yeast and in general salt. In many cases additional ingredients (such as enzymes) are added to improve the quality of the dough or bread. These ingredients can be added separately or added as a premix. Such a premix would be included in the term composition as used in this application.

The lipase may be a plant, animal or microbial lipase, and may be obtained from these sources. Preferably microbial lipase is used. As an example, lipase from *Rhizopus oryzae*, commercially available from Gist-brocades under the trademark Fermizyme L10000, may be used. Other suitable lipases can be obtained from Humicola, Rhizomucor, Candida, Aspergillus, Rhizopus or Pseudomonas species.

Lipase activity can be measured by pH-stat monitoring the production of free fatty acids from olive oil. 1 PLi unit is the amount of enzyme needed to produce 1 $\mu$mole free fatty acid per minute at pH 7.5 and 37 âC from a neutral olive oil/water emulsion.

The following examples illustrate the invention:

EXAMPLE 1

367 kg liquid lipase ultrafiltrate (activity: 17500 PLi/g, dry matter: 135 g/l) was sprayed in a fluidized bed granulator at 40 âC under pressure (4 bars) and with a flow rate of 1300 g/min on 295 kg sieved sodium chloride (granule size: 60 $\mu$m<95%<300 $\mu$m). In the meantime a solution was prepared by mixing 41 kg maltodextrin (DE12, commercially available from ROQUETTE, Lestrem, France) and 2.14 kg Pharmacoat (Hydroxypropyl methylcellulose, commercially available from SEPPIC, Paris, France) in 64 kg demineralized water. This solution was sprayed (after the lipase had been applied to the NaCl carrier) at 40° C. under pressure (4 bars) with a flow rate of 1300 g/min. Continuous air flow (6500 m$^3$/h) was maintained during both spraying operations.

Drying was then carried out by heating at 42° C. for 10 minutes while maintaining the same continuous air-flow (6500 m$^3$/h). The temperature was then finally brought down to 25° C. under continuous air-flow. This yielded 439 kg coated lipase:

activity:
    12700 PLi/g (i.e. enzymatic yield is 87%)
moisture:
    8.1%
granule size distribution:
    125 μm<41%<315 μm
    315 μm<51%<400 μm
thickness coating layer:
    10 μm.

EXAMPLE 2

301 Kg liquid lipase ultrafiltrate (activity: 17500 PLI/g, dry matter: 135 g/l) was sprayed at 40° C. under pressure (5 bars) and with a flow rate of 1300 g/min on 242 kg sieved sodium chloride (granule size: 60 μm<95%<300 μm). In the meantime a solution was prepared by mixing 33 kg maltodextrin and 1.75 kg Pharmacoat in 53 kg demineralized water. This solution was sprayed (after the lipase had been applied to the NaCl carrier) at 40° C. under pressure (5 bars) with a flow rate of 1000 g/min. Continuous air flow (7000 m$^3$/h) was maintained during both spraying operations.

Drying was then carried out by heating at 42° C. for 12 minutes while maintaining the same continuous air-flow (7000 m$^3$/h). The temperature was then finally brought down to 25° C. under continuous air-flow (6500 m$^3$/h). This yielded 361 kg coated lipase:

activity:
    13400 PLi/g (i.e. enzymatic yield is 92%)
moisture:
    7.2%
granule size distribution:
    125 μm<59%<315 μm
    315 μm<37%<400 μm
thickness coating layer:
    10 μm.

EXAMPLE 3

The following two compositions were prepared:

| | | |
|---|---|---|
| Salt | 42% | 42% |
| Hard fat soy 38 | 4.8% | 24% |
| Fat kernels 80% soy fat 38 | 24% | 19% |
| Soy flour | 19% | 9.45% |
| Starch | 9.2% | |
| Fermizyme L10000 | 1% | |
| Coated lipase, 13400 Pli/g | | 0.75% |

These compositions are examples of compositions which may be used to improve the properties of bread.

Fermizyme L10000 is a powder lipase standardized to 10000 PLi/g. The coated lipase is from Example 2.

The compositions were stored at 25° C. Every two to three days the smell of the compositions was judged. The composition containing Fermizyme L10000 started getting rancid after two days. However, in the composition containing coated lipase no rancidity developed within 60 days. The lipase activity was not significantly decreased during storage.

We claim:

1. A bread improver composition comprising a coated lipase granule comprising lipase having a coating, said coating comprises a material which is impervious to lipid wherein said coating has a thickness so dimensioned as to substantially prevent fat degradation during storage and the amount of said coating comprises 1 to 25 w/w % of the coated lipase granule.

2. A bread improver composition according to claim 1 wherein the lipase is present in granular form and coated with the lipid impervious material to form said coated granule.

3. A bread improver composition according to claim 1 wherein the lipase is present on the outer surface of a particle and the lipase coated particle has an outer coat of the lipid impervious material to form said coated granule.

4. A bread improver composition according to claim 1 wherein the lipase has been absorbed by a particle and then coated with the lipid impervious material to form said coated granule.

5. The method as set forth in claim 1, wherein said gas injected into said quartz tube comprises oxygen.

6. A bread improver composition according to claim 1 wherein the lipase is of microbial origin.

7. A method of making a bread improver composition of claim 1, the method comprising coating either (i) either a granule comprising a lipase; or (ii) a carrier particle comprising a lipase, wherein said lipase is coated with a lipid impervious material.

8. A composition according to claim 1 which further comprises fat.

9. A method for hydrolysing a lipid present in a bread dough which comprises adding to said bread dough the bread improver composition of claim 1.

10. A bread dough comprising a bread improver composition as defined in claim 1.

11. A method of making a bread dough comprising adding together water, flour, yeast and a bread improver composition as defined in claim 1 or adding to said bread dough a bread improver composition as defined in claim 1.

12. A method to prevent the occurrence of rancidity when lipase is brought into contact with a fat during storage of a bread improver composition, which comprises coating said lipase with 1–25 w/w % of a fat-impervious material.

13. The method of claim 12 further comprising the step of adding salt.

* * * * *

UNITED STATES PATENT AND TRADEMARK OFFICE
CERTIFICATE OF CORRECTION

PATENT NO. : 6,083,538  
DATED : July 4, 2000  
INVENTOR(S) : Johannes Josef Plijter et al.

Page 1 of 1

It is certified that error appears in the above-identified patent and that said Letters Patent is hereby corrected as shown below:

Column 4,
Lines 34-35, A bread improver composition according to claim 1 wherein the lipase is of microbial origin.
Lines 36-37, A method of making a bread improver composition of claim 1, the method comprising coating either (I) either a granule comprising a lipase; or (ii) a carrier particle comprising a lipase, wherein said lipase is coated with a lipid impervious material.
Lines 38-42, A composition according to claim 1 which further comprises fat.
Lines 43-44, A method for hydrolysing a lipid present in a bread dough which comprises adding to said bread dough the bread improver composition of claim 1.
Lines 45-47, A bread dough comprising a bread improver composition as defined in claim 1.
Lines 48-49, A method of making a bread dough comprising adding together water, flour, yeast and a bread improver composition as defined in claim 1 or adding to said bread dough a bread improver composition as defined in claim 1.
Lines 50-53, A method to prevent the occurrence of rancidity when lipase is brought into contact with a fat during storage of a bread improver composition, which comprises coating said lipase with 1-25 w/w % of a fat-impervious material.
Lines 54-57, The method of claim 11 further comprising the step of adding salt.

Signed and Sealed this

Fourteenth Day of May, 2002

*Attest:*

*Attesting Officer*

JAMES E. ROGAN  
*Director of the United States Patent and Trademark Office*